US011406090B2

United States Patent
Zhang et al.

(10) Patent No.: US 11,406,090 B2
(45) Date of Patent: Aug. 9, 2022

(54) METHOD OF PREPARING DDX27-DELETION ZEBRAFISH MUTANTS

(71) Applicant: Shanghai Ocean University, Shanghai (CN)

(72) Inventors: Qinghua Zhang, Shanghai (CN); Can Shi, Shanghai (CN)

(73) Assignee: Shanghai Ocean University, Shanghai (CN)

( * ) Notice: Subject to any disclaimer, the term of this patent is extended or adjusted under 35 U.S.C. 154(b) by 517 days.

(21) Appl. No.: 16/421,460

(22) Filed: May 23, 2019

(65) Prior Publication Data
US 2020/0053990 A1 Feb. 20, 2020

(30) Foreign Application Priority Data
May 28, 2018 (CN) .......................... 201810525964.6

(51) Int. Cl.
*C12N 15/88* (2006.01)
*A01K 67/027* (2006.01)
*C12N 15/90* (2006.01)

(52) U.S. Cl.
CPC ........ *A01K 67/0276* (2013.01); *C12N 15/902* (2013.01); *A01K 2207/15* (2013.01); *A01K 2217/056* (2013.01); *A01K 2217/075* (2013.01); *A01K 2227/40* (2013.01); *A01K 2267/03* (2013.01)

(58) Field of Classification Search
CPC .................................................. A01K 67/0276
See application file for complete search history.

(56) References Cited

PUBLICATIONS

Bennett et al. "RNA helicase, DDX27 regulates skeletal muscle growth and regeneration by modulation of translational processes." PLoS genetics 14.3 (2018): e1007226 (Year: 2018).*
Yu et al. "Zebrafish androgen receptor is required for spermatogenesis and maintenance of ovarian function." Oncotarget 9.36 (2018): 24320 (Year: 2018).*
Buck et al. "Design strategies and performance of custom DNA sequencing primers." Biotechniques 27.3 (1999): 528-536 (Year: 1999).*
Xie et al. sgRNAcas9: a software package for designing CRISPR sgRNA and evaluating potential off-target cleavage sites. PloS one 9.6 (2014): e100448 (Year: 2014).*
Sequence Search Report Result 3, Accession No. CU929339, Submitted by Wellcome Trust Sanger Institute on Dec. 13, 2012 (Year: 2012).*

* cited by examiner

*Primary Examiner* — Christopher M Babic
*Assistant Examiner* — Alexander W Nicol

(57) ABSTRACT

A method of preparing a ddx27-deletion zebrafish mutant, including: determining a target of ddx27 knockout on a sixth exon of the ddx27 in a zebrafish and designing a gRNA sequence; using primers T7-ddx27-sfd and tracr rev for PCR amplification with a pUC19-gRNA scaffold plasmid as a template; purifying and transcribing the PCR product obtained in vitro to produce gRNA; introducing the gRNA and a Cas9 protein into the zebrafish; and culturing the zebrafish to obtain a zebrafish ddx27 mutant of stable inheritance. In addition, the application also discloses a phenotype of the ddx27-deletion zebrafish mutant, which plays an important role in investigating the biological function.

6 Claims, 7 Drawing Sheets

Specification includes a Sequence Listing.

SEQUENCE LISTING

<160> NUMBER OF SEQ ID NOS: 7

<210> SEQ ID NO 1
<211> LENGTH: 20
<212> TYPE: DNA
<213> ORGANISM: Danio rerio

```
<400> SEQUENCE: 1
ggacagattc atgtcctgga                                                20

<210> SEQ ID NO 2
<211> LENGTH: 56
<212> TYPE: DNA
<213> ORGANISM: Artificial Sequence
<220> FEATURE:
<223> OTHER INFORMATION: synthetic

<400> SEQUENCE: 2
aatacgactc actataggac agattcatgt cctggagttt tagagctaga aatagc       56

<210> SEQ ID NO 3
<211> LENGTH: 25
<212> TYPE: DNA
<213> ORGANISM: Artificial Sequence
<220> FEATURE:
<223> OTHER INFORMATION: synthetic

<400> SEQUENCE: 3
aaaaaaagca ccgactcggt gccac                                         25

<210> SEQ ID NO 4
<211> LENGTH: 20
<212> TYPE: DNA
<213> ORGANISM: Artificial Sequence
<220> FEATURE:
<223> OTHER INFORMATION: synthetic

<400> SEQUENCE: 4
gaaaggaaag aggaaaatgg                                                20

<210> SEQ ID NO 5
<211> LENGTH: 20
<212> TYPE: DNA
<213> ORGANISM: Artificial Sequence
<220> FEATURE:
<223> OTHER INFORMATION: synthetic

<400> SEQUENCE: 5
ttcgttgttt gattcctatt                                                20

<210> SEQ ID NO 6
<211> LENGTH: 120
<212> TYPE: DNA
<213> ORGANISM: Danio rerio

<400> SEQUENCE: 6
taatacgact cactataggc atctgcatga atacacagtt ttagagctag aaatagcgga   60
cagattcatg tcctggacgt tatcaacttg aaaaagtggc accgagtcgg tgcttttttt  120

<210> SEQ ID NO 7
<211> LENGTH: 83
<212> TYPE: DNA
<213> ORGANISM: Artificial Sequence
<220> FEATURE:
<223> OTHER INFORMATION: synthetic

<400> SEQUENCE: 7
gttttagagc tagaaatagc aagttaaaat aaggctagtc cgttatcaac ttgaaaaagt   60
ggcaccgagt cggtgctttt ttt                                           83
```

METHOD OF PREPARING DDX27-DELETION ZEBRAFISH MUTANTS

REFERENCE TO AN ELECTRONIC SEQUENCE LISTING

The contents of the electronic sequence listing (Untitled_ST25_20191107.txt; Size: 2,000 bytes; and Date of Creation: Nov. 7, 2019) is herein incorporated by reference in its entirety.

CROSS-REFERENCE TO RELATED APPLICATIONS

This application claims the benefit of priority from Chinese Patent Application No. 201810525964.6, filed on May 28, 2018. The content of the aforementioned application, including any intervening amendments thereto, is incorporated herein with reference in its entirety.

TECHNICAL FIELD

The application relates to molecular biology, and more particularly to a method of preparing ddx27-deletion zebrafish mutants using CRISPR/Cas9 gene editing techniques.

BACKGROUND

Clustered regularly interspaced short palindromic repeat/CRISPR-associated genes (CRISPR/Cas) system is an adaptive immune defense mechanism in bacteria and archaea, which is derived from the evolution of organism and plays a role in protecting the genome of an organism from being interfered with exogenous nucleic acids. In 1987, the CRISPR and the Cas genes were discovered near the alkaline phosphatase gene of E. coli K12 by researchers from Osaka University. CRISPR RNA (crRNA) guides the Cas protein by base complementation to recognize the invading exogenous genome and digest the DNA. The CRISPR/Cas system can be classified into type I, type II and type III according to the sequence and structure of the Cas protein, where the type I and type II CRISPR-Cas systems can degrade exogenous DNA, while the type ITT CRISPR-Cas system, in addition to degrading exogenous DNA, can also degrade exogenous RNA. In addition, the degradation of exogenous nucleic acids mediated by the type I and type III CRISPR-Cas systems requires the involvement of multiple Cas proteins, while only a single Cas9 protein is required in the degradation mediated by the type II CRISPR-Cas system, which enables rapid and wide application of Cas9 in the biological field. The type II CRISPR/Cas system, i.e., the CRISPR/Cas9 system, has been developed into a desirable programmatic gene editing tool. There are two successive steps necessary in the Cas9-mediated gene editing. First, the genome DNA is digested by the Cas9 endonuclease under the mediation of crRNA, and then, the DNA DSB (double strand break) is repaired by the intracellular natural DNA repair system.

Compared to the conventional gene editing techniques, the CRISPR/Cas9 has higher efficiency and simpler operation. Specifically, the CRISPR/Cas9 has the following advantages.

1. Since the Cas protein is nonspecific, it is only required to synthesize one gRNA to specifically modify the gene.

2. It is easy to construct a gRNA-encoding sequence due to a length equal to 150 bp or less.

3. A shorter gRNA sequence also avoids the adverse effects of the long encoding vector on the organism.

It has been demonstrated that the DExD/H-box family is involved in various aspects of RNA metabolism as a member of the RNA helicase superfamily and is present in most organisms which have a RNA helicase or ribonucleoprotein (RNP) enzyme activity. In addition, in the cell, the DExD/H-box family can hydrolyze nucleotide triphosphate (NTP) and can form a complex with other proteins to exert functions. The DExD/H-box family plays an important role in almost all cellular processes involving RNA, such as transcription, mRNA precursor splicing, mRNA export, ribosome formation, translation initiation, organelle gene expression, RNA degradation, etc., affecting the RNA synthesis and polymorphisms. However, the in-vivo characteristics and the specific function of these enzymes are still less explored.

Based on the analysis of extensive clinical tumor cases, it has been found that the DDX27 is highly expressed in cancerous tissues to promote the cell proliferation and the colony formation, suitable for the potential target of a therapeutic drug. The application employs a model organism zebrafish and genetically edits its genome using the CRISPR/Cas9 technique to achieve the positioning knockout of the target gene, thereby generating a ddx27 gene-deletion mutant, which provides support for the subsequent researches on the molecular mechanism and application in disease modeling.

SUMMARY

An object of the application is to provide a method of preparing a ddx27-deletion zebrafish mutant. In this application, a novel target sequence of gRNA is designed at the sixth exon of the ddx27 and is shown as GGACAGATTCATGTCCTGGA, by which the ddx27 gene can be knocked out.

The technical solutions of the application are described as follows.

The application discloses a method of preparing a ddx27-deletion zebrafish mutant, comprising:

(1) determining a target of ddx27 knockout on a sixth exon of the ddx27 in a zebrafish and designing a gRNA sequence;

(2) designing and synthesizing an upstream primer T7-ddx27-sfd and a downstream primer tracr rev;

(3) using primers T7-ddx27-sfd and tracr rev for PCR amplification with a pUC19-gRNA scaffold plasmid as a template;

(4) transcribing and transforming the PCR product obtained in step 3 in vitro to produce gRNA;

(5) introducing the gRNA and a Cas9 protein into the zebrafish; and (6) culturing the zebrafish obtained in step 5 to obtain a zebrafish ddx27 mutant.

In an embodiment, in step 1, the target has a sequence shown as SEQ ID NO.1.

In an embodiment, in step 2, an upstream primer $F_1$ (T7+Target site+scaffold), i.e., the primer T7-ddx27-sfd, has a sequence shown as TAATACGACTCACTATAGGACAGATTCATGTCCTGGA GTTTTAGAGCTAGAAATAGC (SEQ ID NO.2); and a downstream primer $R_1$ (trans reverse), i.e., the primer tracr rev, has a sequence shown as AAAAAAAGCACCGACTCGGTGCCAC (SEQ ID NO.3).

In an embodiment, in step 3, the pUC19-gRNA scaffold plasmid has a sequence shown as GTTTTAGAGCTAGAAATAGCAAGTTAAAATAAGGCTAGTCCGTTATCAACTTGAAAAAGTGGCACCGAGTCGGTGCTTTTTTT (SEQ ID NO.7).

In an embodiment, in step 4, the gRNA has a sequence shown as TAATACGACTCACTATAGGCATCTGCATGAATACACAGTTTTAGAGCTAGAA ATAGCGGACAGATTCATGTCCTGGACGTTATCAACTTGAAAAAGTGGCACC GAGTCGGTGCTTT (SEQ TD NO.6).

In an embodiment, step 5 further comprises:

mixing the gRNA with the Cas9 protein to produce a mixture and microinjecting the mixture into a 1-cell stage embryo of the zebrafish; wherein a final concentration of the gRNA is 80-100 ng/μL; a final concentration of the Cas9 protein is 800 ng/μL; and a total volume of the mixture is 1 μL.

In an embodiment, step 6 further comprises:

(i) examining embryos of the zebrafish introduced with the gRNA and the Cas9 protein and a wild-type zebrafish to measure ddx27 knockout efficiency so as to determine that an $F_0$ ddx27-knockout zebrafish is cultured to be an adult zebrafish;

(ii) outcrossing the adult $F_0$ ddx27-knockout zebrafish with the wild-type zebrafish to test heritability and effective mutations, thereby screening an $F_1$ zebrafish with heritable and effective mutation for feeding to adult zebrafish; wherein an $F_1$ zebrafish ddx27 mutant is obtained by genotype identification;

(iii) incrossing the same $F_1$ zebrafish ddx27 mutants to obtain an $F_2$ zebrafish ddx27 mutant; and (iv) identifying the homozygous $F_2$ zebrafish ddx27-knockout mutant as the zebrafish ddx27 mutant of stable inheritance.

In an embodiment, in step (i), the ddx27 knockout is examined by using a primer sequence comprising an upstream primer ddx27-F of a sequence shown as GAAAGGAAAGAGGAAAATGG (SEQ ID NO.4) and a downstream primer ddx27-R of a sequence shown as TTCGTTGTTTGATTCCTATT (SEQ ID NO.5).

In an embodiment, step 6 further comprises:

(iv) examining whether the gene to be knocked out of a parental zebrafish is homozygous;

(iv-a) designing primers around the target to make them more than 100 bp away from both sides of the target and to ensure the absolute value of the difference between the distances of the primers from the target to be greater than 100 bp;

(iv-b) selecting a pair of healthy WT zebrafish as the parent; cutting their tails for PCR; and directly subjecting the resulting PCR product to sequencing;

(iv-c) requiring the target sequence of the experimental material (the adult zebrafish to be injected) to be homozygous (determined by analyzing the peak map); if the sequencing results show that the target sequence is heterozygous, the experimental material needs to be reselected;

(v) microinjection: mixing the gRNA and the Cas9 protein and introducing the mixture into the zebrafish; where a final concentration of the gRNA is 80-100 ng/μl.,; a final concentration of the Cas9 protein is 800 ng/μL; and a total volume of the mixture is 1 μL;

(vi) on the evening of the injection day, picking out the dead eggs and replacing half of the water; then replacing the water every morning and evening; after fertilization for 48 hours, determining whether the knockout is successful using T7E1 enzyme assay and feeding the $F_0$ zebrafish involving successful knock out;

(vii) after feeding for 3-4 months, when the sexual maturity of the zebrafish is reached, crossing the $F_0$ zebrafish mutant with the wild-type zebrafish to obtain a heterozygote with a certain probability; collecting embryos for genome extraction; performing PCR with the detection primers; treating the PCR product using TA cloning followed by sequencing to determine the genotype; and identifying the $F_1$ zebrafish involving heritable and effective mutation for feeding; and (vii) after feeding for 3-4 months, when the sexual maturity of the zebrafish is reached, subjecting the male and female $F_1$ adult zebrafish mutants to tail cutting for identification and screening of the genotype; mating the zebrafish mutants again to obtain the homozygous ddx27 gene-deletion zebrafish mutant.

Compared to the prior art, the application has the following beneficial effects.

1) The application first employs the CRISPR/Cas9 technique to design a specific targeting site, achieving the specific knockout of the ddx27 gene in zebrafish. The ddx27 encodes a total of 776 amino acids while the mutant with 27 bp deletion encodes 208 amino acids. Moreover, the mutants with 14 bp deletion and 5 bp deletion encode 233 amino acids and 236 amino acids, respectively.

2) The ddx27 mutation can facilitate the further research on the functional mechanism of the ddx27 due to the desirable genetic stability.

3) Zebrafish mutants of different ddx27$^{-/-}$ mutation types all show homozygous lethality, and all dies about 6-7 days post fertilization (dpf).

4) Severe phenotype is observed in zebrafish ddx27$^{-/-}$ mutants and obvious development delay and deformity such as small head, small eyes and pericardical edema are observed 3 dpf.

BRIEF DESCRIPTION OF THE DRAWINGS

FIG. 1 shows the examination of ddx27 knockout in an $F_0$ zebrafish, where

FIGS. 2A and 2B show gel electrophoresis results of digestion by T7E1 endonuclease; and FIG. 2C is a peak map showing the sequencing results of PCR products.

FIG. 3A shows part of the gel electrophoresis results of digestion by T7E1 endonuclease; and FIG. 3B shows alignment results of sequencing of monoclones selected by ligation and transformation of PCR products.

FIG. 4A is a statistical histogram showing proportions of various phenotypes of ddx27-27 bp; FIG. 4B is a statistical histogram showing proportions of various phenotypes of ddx27-14 bp; and FIG. 4C is a statistical histogram showing proportions of various phenotypes of ddx27-5 bp.

FIG. 5A shows comparison between the ddx27-27 bp mutant and the wild-type zebrafish in phenotype (3 dpf); FIG. 5B shows comparison between the ddx27-14 bp zebrafish mutant and the wild-type zebrafish in phenotype (3 dpf); FIG. 5C shows comparison between the ddx27-5 bp zebrafish mutant and the wild-type zebrafish in phenotype (3 dpf); FIG. 5D shows comparison between 10 ddx27-27 bp zebrafish mutants and 10 wild-type zebrafish in phenotype (3 dpf); FIG. 5E shows comparison between 10 ddx27-14 bp zebrafish mutants and 10 wild-type zebrafish in phenotype (3 dpf); and FIG. 5F shows comparison between 10 ddx27-5 bp zebrafish mutants and 10 wild-type zebrafish in phenotype (3 dpf).

DETAILED DESCRIPTION OF EMBODIMENTS

Figure 1A:
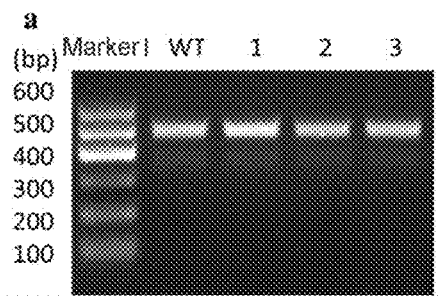
FIG. 1A shows gel electrophoresis results of PCR product from the ddx27 of an $F_0$ zebrafish embryo.

The invention will be illustrated in detail below with reference to the embodiments. The following embodiments will help those skilled in the art further understand the invention, but are not intended to limit the invention in any way. It should be noted that some adjustments and improvements made by those skilled in the art without departing from the spirit should still fall within the scope of the invention.

EXAMPLE 1

1 Materials and Instruments 1.1 Experimental Sample

Zebrafish used herein were all derived from the AB strain and were purchased from the Zebrafish Platform of Shanghai Institute of Biochemistry and Cell Biology, Chinese Academy of Sciences.

1.2 Plasmid

The pUC19-gRNA scaffold plasmid was referred to a literature (Chang N, Sun C, Gao L, Zhu D, Xu X, Zhu X, Xiong J W, Xi J J. Genome editing with RNA-guided Cas9 nuclease in zebrafish embryos, Cell Res, 2013, 23 (4):465-472).

The pUC19-gRNA scaffold plasmid was used as a template in the synthesis of gRNA product and had a sequence shown in GTTTTAGAGCTAGAAATAGCAAGT-TAAAATAAGGCTAGTCCGTTATCAACTT GAAAAAGTGGCACCGAGTCGGTGCTTTTTT (SEQ ID NO.7).

1.3 Reagent

DNA Clean & Contentrator-5 (ZYMO RESEARCH, D4004); Ordinary DNA purification kit (TIANGEN BIOTECH CO., Ltd., DP204-03); MAXIscriptt® T7 in vitro Transcription Kit (Ambion, AM1314); Absolute ethanol (Sinopharm Chemical ReagentCo., Ltd., 10009218); GenCrispr NLS-Cas9-NLS (GenScript, Z03389-25); Premix Taq™ (Ex Taff Version 2.0 plus dye) (TAKARA, RR902); DNA Marker I (TIANGEN BIOTECH CO., Ltd, MD101-02); T7endonuclease 1 (NEW ENGLAND BioLab® Inc., M0302L); Rapid Plasmid Miniprep kit (TIANGEN BIOTECH CO., Ltd, DP105); DH5a competent cells (TIANGEN BIOTECH CO., Ltd, CB101-03); 2BEasyTaq PCR SuperMix (+dye) (TAKARA, AS111-12); LB Broth (Sangon Biotech (Shanghai) Co., Ltd., D915KA6602); LB Broth agar (Sangon Biotech (Shanghai) Co., Ltd, D911KA6566); and pMD™ 19-T Vector Cloning Kit (TAKARA, 6013).

1.4 Instruments

PCR instrument (BIO-RAD, cl 000 Touch™ Thermal Cycler); Small centrifuge (eppendorf, Centrifuge 5424); Vortex mixer (VORTEX-GENIE, G560E); UV spectrophotometer (Thermo Scientific, Nanodrop 2000C); Electrophoresis apparatus (BIO-RAD, PowerPac Basic); Gel imager (Bio-Rad, Gel Doc EZ Imager); Electronic balance (METTLER TOLEDO, AL104); Glass capillary (WPI, TW100E-4); Milli-Q Direct 8 Ultra-pure Water System (Millipore, Milli-Q Direct 8); Vertical puller (NARISHIGE, PC-10); Thermostatic shaker (Innova, 40R); Microgrinder (NARISHIGE, EG-400); Micro syringe pump (WARNER, PLI-100A); Thermostatic water bath (Shanghai Jing Hong Laboratory Instrument Co., Ltd., H1401438, DK-8D); 4° C. Refrigerator (Haier, HYC-610); −40° C. Low-temperature refrigerator (Haier, DW-40L508); -80° C. Ultra-low temperature freezer (Panasonic, MDF-U53V); and High-Pressure Steam Sterilization Pot (SANYO Electric Co., Ltd., MLS-3780).

2. Method 2.1 Synthesis of gRNA (1) Design of Target a. Downloading of Sequence

The Ensembl database was searched and the sequence of ddx27 in the zebrafish was downloaded.

b. Design of Target

The target was designed at the exon sequence following ATG of the ddx27 gene using the website http://zifit.partners.org/ZiFiT/ChoiceMenu.aspx (Table 1). The target of the ddx27 was designed at the sixth exon.

c. Detection for the Specificity of the Target

The designed target sequence was verified for the specificity by blast alignment on the NCBI website.

d. Detection of Parents

The tail of the WT zebrafish for gene knocking out was cut and lysed with a base to obtain the genomic DNA. The genomic DNA was then used to amplify a sequence near the target by PCR.

e. Detection of Digestion

The WT zebrafish was treated with T7E1 endonuclease to determine whether the T7E1 enzyme can digest the amplified fragment. If the fragment cannot be digested, the T7E1 enzyme was suitable for the subsequent detection of knockout, and if the fragment was digested, it is required to select a specific enzyme for digestion detection based on amplified sequence.

f. Identification by Sequencing

The PCR products were sequenced. By alignments of peak maps and sequences, the parents were confirmed to be homozygous and no natural mutation occurred, thus ensuring that the subsequently prepared mutants were generated by gene knockout.

TABLE 1

Target sequence of ddx27

| Gene | Chromo-some | Full length/bp | Length of mRNA/bp | Number of amino acids/aa | Number of introns | Number of exons | Target sequence (5'-3') | Exon |
|---|---|---|---|---|---|---|---|---|
| ddx27 | 6 | 41352 | 2626 | 776 | 20 | 21 | GGACAGATTCATGTCCTGGA (SEQ ID NO. 1) | 6 |

(2) Design of the Primers for Detection

It should be ensured that the designed primers were greater than 100 bp away from both sides of the target. Moreover, the difference between the distance between the upstream primer and the target and the distance between the downstream primer and the target were preferably greater than 100 bp, at least 50 bp. The primers used for amplification should be specific and the amplified fragment had a length of about 500 bp. The primers were synthesized by Sangon Biotech (Shanghai) Co., Ltd. (Table 2).

TABLE 2

Information about primers used in the experiment

| Primers | Sequence (5'-3') | Full length/bp | Length of the digested fragments/bp |
|---|---|---|---|
| T7-ddx27-sfd | AATACGACTCACTATAGGACAGATTCATGTCCTGGAGTTTTAGAGCTAGAAATAGC (SEQ ID NO. 2) | 120 | — |
| trac rev | AAAAAAAGCACCGACTCGGTGCCAC (SEQ ID NO. 3) | — | — |
| ddx27-F | GAAAGGAAAGAGGAAAATGG (SEQ ID NO. 4) | 487 | 190 + 297 |
| ddx27-R | TTCGTTGTTTGATTCCTATT (SEQ ID NO. 5) | | |

(3) Synthesis of gRNA Product

The pUC19-gRNA scaffold plasmid was used as a template, and the fragment was amplified using primers T7-ddx27-sfd and tracr rev and 2×EasyTaq PCR SuperMix (+dye), and purified using a kit.

(4) In-Vitro Transcription

The reaction system was shown in Table 3.

TABLE 3

| | |
|---|---|
| Nuclease-free Water | to 20 μL |
| DNA template | 1 μg |
| 10 × Transcription Buffer | 2 μL |
| 10 mM ATP | 1 μL |
| 10 mM CTP | 1 μL |
| 10 mM GTP | 1 μL |
| 10 mM UTP | 1 μL |
| T7Enzyme Mix | 2 μL |

It should be noted that 10×Transcription Buffer and T7Enzyme Mix were finally added.

The reaction system was mixed uniformly, centrifuged for a short time and incubated at 37° C. for 80 minutes. The reaction system was further added with TURBO DNase (1 μL), mixed uniformly, centrifuged for a short time and incubated at 37° C. for 15 minutes.

(5) Purification of gRNA a. To the in-vitro transcription system (20 μL) were added LiCl (2.5 μL, 4 M) and absolute ethanol (100 μL). The reaction system was mixed uniformly, centrifuged for a short time and placed in the −80° C. freezer for at least 1 hour.

b. Then the reaction system was transferred from the freezer and centrifuged at 4° C. and 12,000 rpm for 15 minutes. The supernatant was discarded, and the precipitate was washed with 70% ethanol and centrifuged at 4° C. and 8,000 rpm for 5 minutes. The supernatant was discarded and the centrifuge tube was transferred to a fume hood to allow the complete evaporation of ethanol.

c. Based on the amount of the precipitate, an appropriate amount of DEPC water was added to dissolve the gRNA precipitate.

d. Concentration and OD value were measured using the Nanodrop, and length of the sequence was detected by electrophoresis.

The gRNA had a sequence shown in TAATACGACTCACTATAGGCATCTGCATGA ATACACAGTTTTAGAGCTAGAA ATAGCGGACAGATTCATGTCCTGGACGTTATCAACTTGAAAAAGTGGCACC GAGTCGGTGCTTTTTTT (SEQ ID NO.6).

2.2 Microinjection

The gRNA was mixed with the Cas9 protein (GenCrispr NLS-Cas9-NLS, GenScript Biotech Co., Ltd., Z03389-25) and injected into the one-cell stage embryo zebrafish by a microinjector. In each injection, some uninjected embryos of the same batch were left and used as the control group. Final concentrations of the gRNA and the Cas9 protein after mixing were 100 ng/μL and 800 ng/μL, respectively.

2.3 Verification of Knockout and Determination of Knockout Efficiency (T7E1 Digestion Test)

a. Extraction of Genome from Zebrafish Eggs 5 eggs in each group were added with NaOH (3.5 μL, 50 mM) and incubated at 95° C. for 20 minutes. During the incubation, the eggs were shaken and centrifuged for a short time once. Then the eggs were added with Tris·HCl (3.5 μL, 1M, pH≈8.0), shaken vigorously for uniform mixing, and centrifuged.

b. PCR Amplification of the Target Fragment

The target fragment was amplified according to the primers designed near the target.

The PCR reaction system was shown in Table 4.

TABLE 4

| | |
|---|---|
| H₂O | to 25 μL |
| Enzyme | 12.5 μL |
| F | 0.5 μL |
| R | 0.5 μL |
| Template | 10 ng |

The PCR reaction conditions were described as follows: pre-denaturation at 98° C. for 2 seconds; 32 cycles with each cycle consisting of denaturation at 98° C. for 10 seconds, annealing at 60.3° C. for 30 seconds and extension at 72° C. for 1 minute; extension at 72° C. for 5 minutes; and storage at 4° C.

The electrophoresis was performed using 2% agarose gel at 120 V for 25 minutes.

c. Detection of T7E1 Endonuclease Digestion

TABLE 5

| | |
|---|---|
| H₂O | to 10 μL |
| PCR product | 5 μL |
| Buffer | 1.1 μL |

The reaction system was incubated at 95° C. for 5 minutes, cooled to room temperature, added with the T7E1 endonuclease (0.25 μL) and incubated at 37° C. for 45 minutes.

d. Detection by Electrophoresis

After electrophoresis, the agarose gel was imaged by a gel electrophoresis imager, and the target band was observed to determine whether the knockout was successful.

2.4 Identification of Genotypes of Homozygous Zebrafish ddx27 Mutants

Genotypes of zebrafish of different deletion types were screened and identified.

Figure 1B:
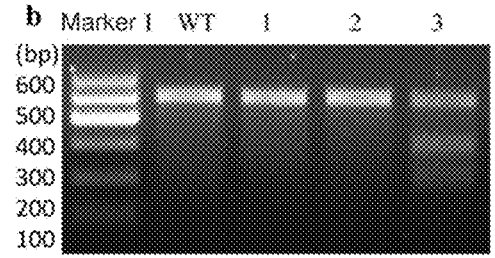
FIG. 1B shows gel electrophoresis results of digestion by T7E1 endonuclease.
Figure 1C:
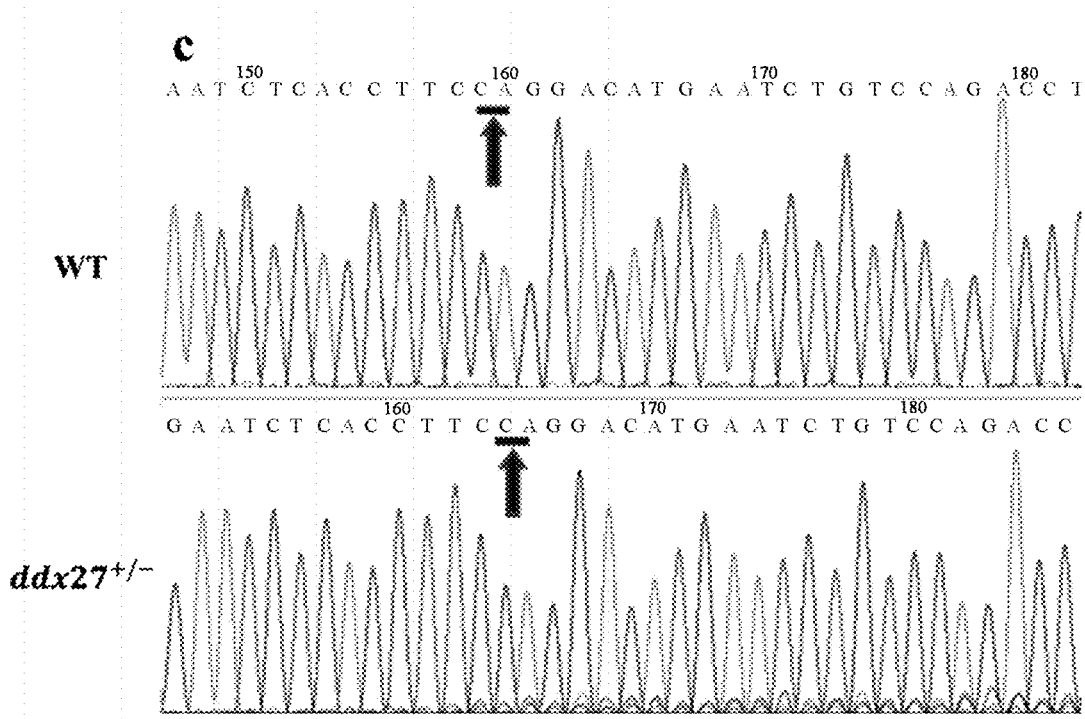
FIG. 1C is a peak map showing the sequencing results of PCR products.

3. Results 3.1 Construction of ddx27 Mutant 3.1.1 Test Results of ddx27 Knockout in $F_0$ Zebrafish The results of T7E1 digestion demonstrated the successful knockout of ddx27. The sequencing peak map showed the presence of overlapping peaks at the target, demonstrating that the ddx27 was knocked out (FIGS. 1A-1C).

3.1.2 Test Results of Germline Transmission of ddx27 in $F_0$ Zebrafish

Figure 2A:
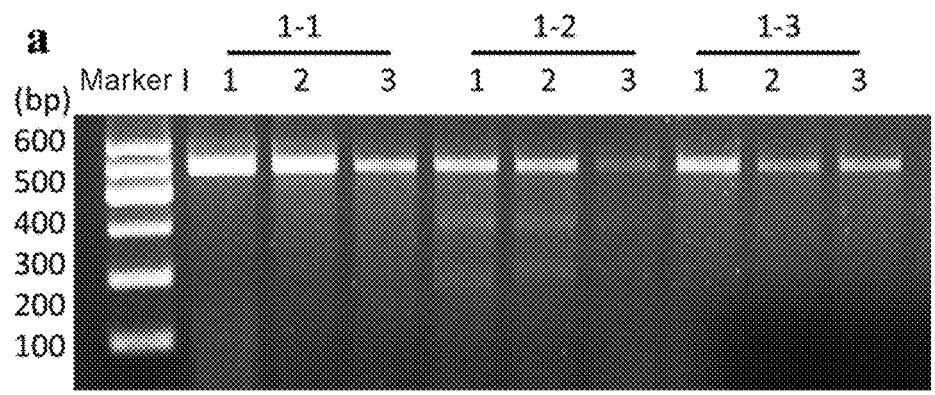
FIGS. 2A-C show the germline transmission test results of the ddx27 of $F_0$ zebrafish, where
Figure 2B:
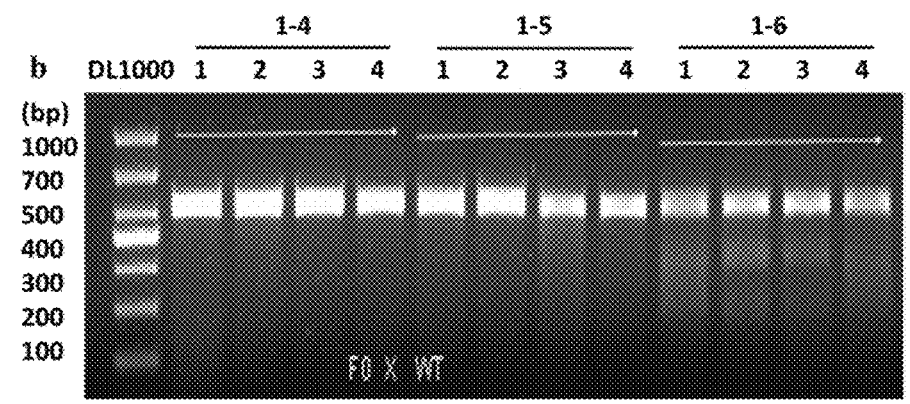
Figure 2C:
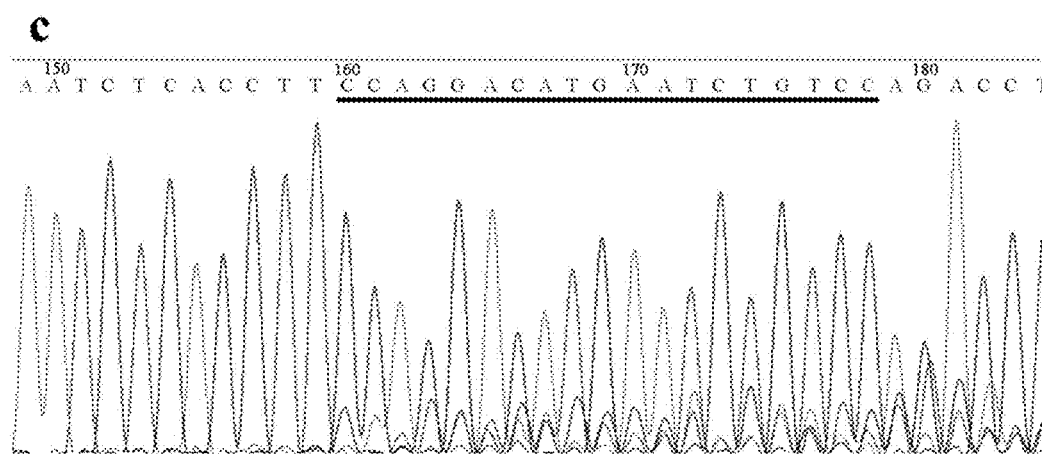

6 $F_0$ adult zebrafish which were detected to involve successful knockout of ddx27 were outcrossed with the wild-type zebrafish to generate $F_1$ embryos and 5 embryos in one tube. 3-4 tubes of embryos were digested by T7E1 endonuclease for identification. The digestion results indicated that the mutation in 2 zebrafish was passed to the offspring (FIGS. 2A-2C).

3.1.3 Identification of Phenotype of $F_1$ Heterozygous Zebrafish ddx27 Mutant 72 zebrafish obtained by outcrossing were detected for their ddx27 gene using tail-cutting method. As shown in the detection results of the T7E1 digestion, 22 positive zebrafish were generated, which were then subjected to TA cloning to determine the occurrence of effective mutation.

Figures 3A, 3B:
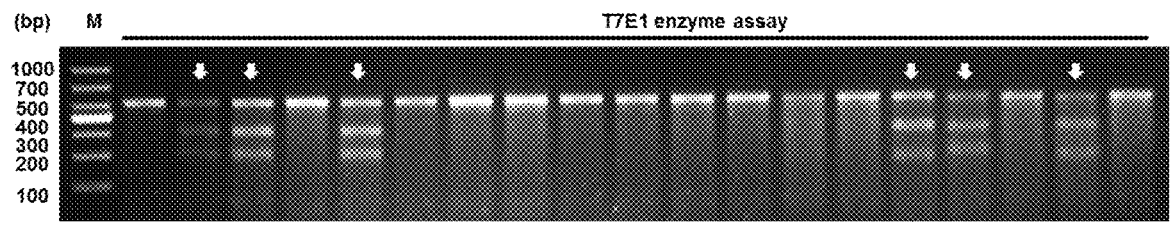
FIGS. 3A-B show the genotype detection results of the ddx27 in an $F_1$ adult zebrafish, where

Among the 22 zebrafish involving effective mutation, after screening, there were 5 mutants involving 27 bp deletion, 13 mutants involving 14 bp deletion and 4 mutants involving 5 bp deletion (FIGS. 3A-3B).

Figure 4A:
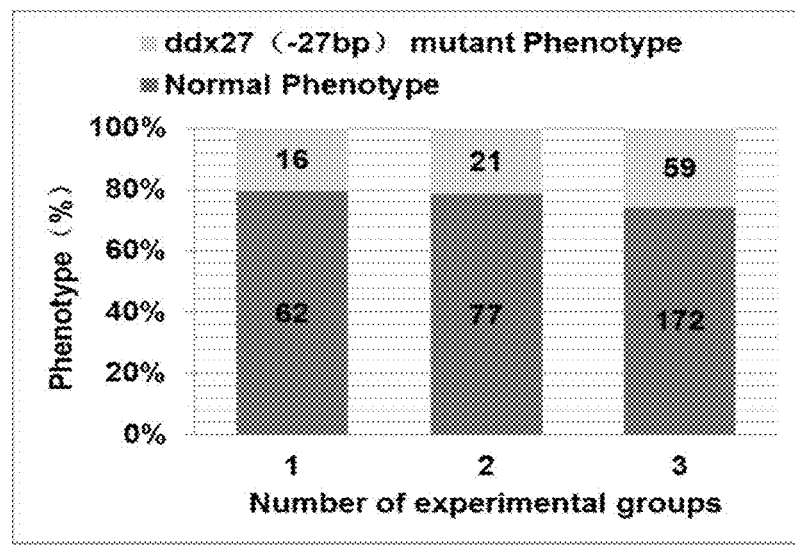
FIGS. 4A-C show statistical results of phenotypes of mutants of different ddx27 deletion types (P value is greater than 0.05 as demonstrated by chi-square test, so that the difference is not significant which is consistent with Mendel's law of inheritance), where
Figure 4B:
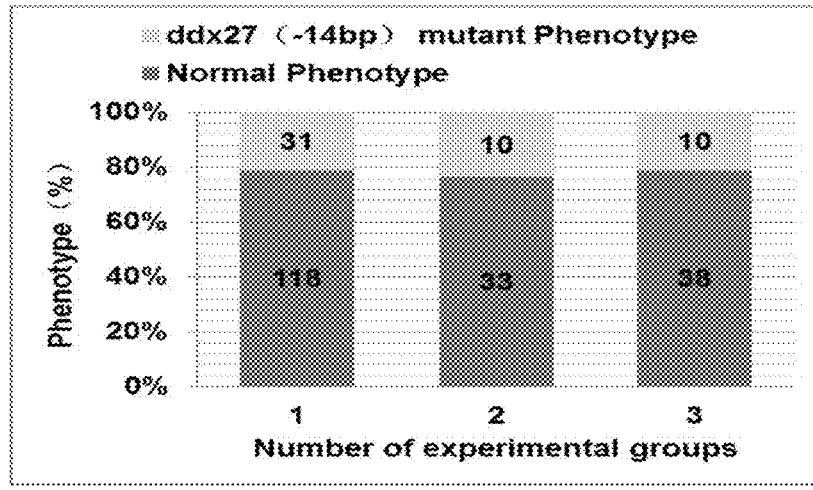
Figure 4C:
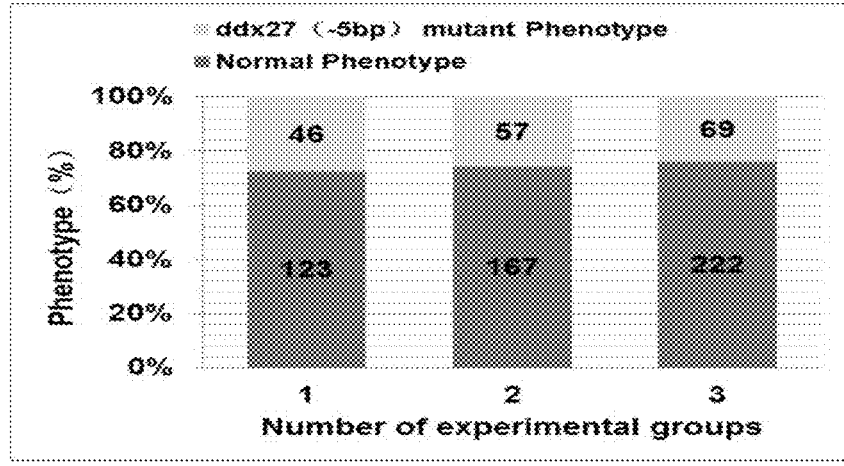
Figures 5A, 5B, 5C:
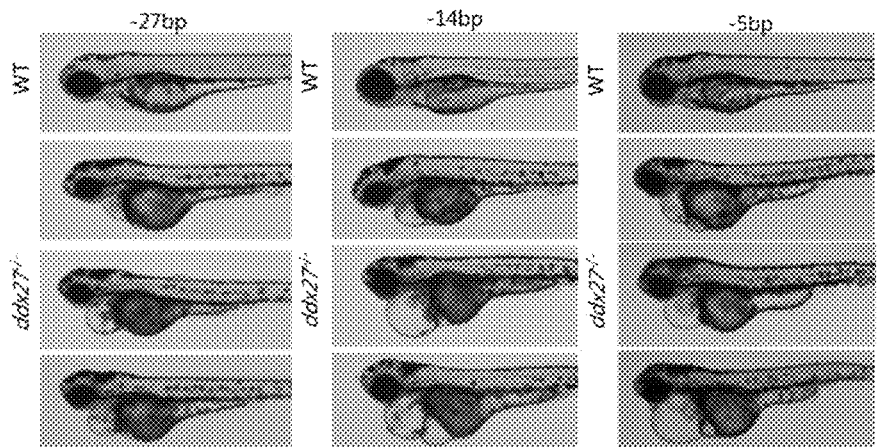
FIGS. 5A-F show comparison between zebrafish mutants of different ddx27 deletions and wild-type zebrafish in phenotype (3 days post fertilization, dpf), where
Figure 5D:
Figure 5E:
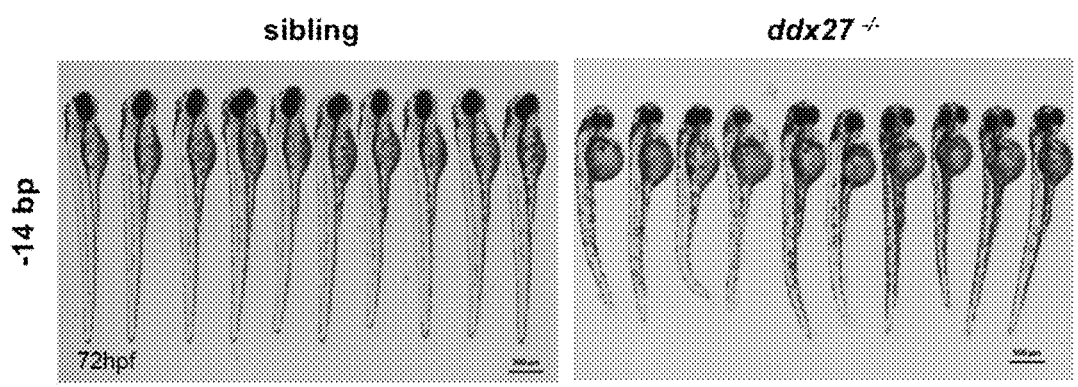
Figure 5F:
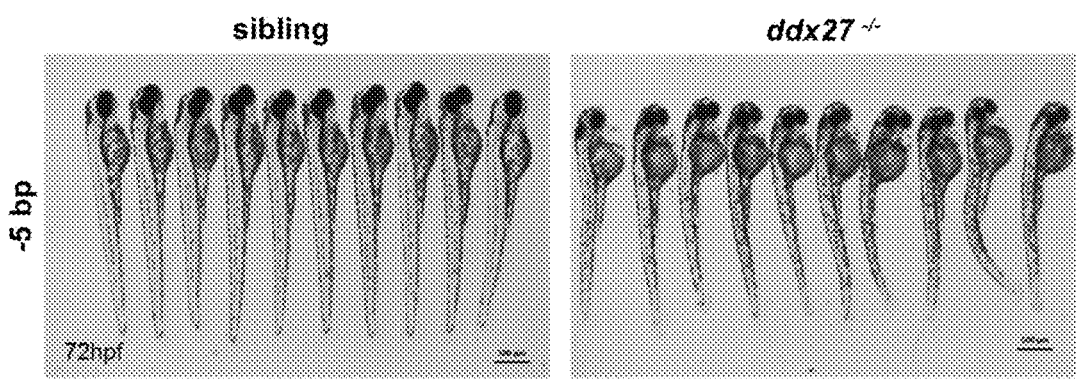

3.1.4 Observation and Photographing of Phenotype of $F_2$ Zebrafish ddx27 Mutant (1) The heterozygous mutants of different ddx27 deletion types were incrossed, and the eggs were collected and cultured for observation of early embryo development. Obvious developmental delays and deformities such as small head, small eyes and pericardical edema were observed 3 days post fertilization. In each mutation type, 3 pairs of different heterozygous mutants were used as parents for spawning, and the numbers of abnormal phenotype and its siblings were counted for chi-square test. The results showed that the difference among the three mutation types was not significant, which was consistent with Mendel's law of inheritance (FIGS. 4A-4C).

(2) To further determine the phenotypes of the ddx27 mutants, the zebrafish mutants of different ddx27 deletion types and the wild-type zebrafish (3 dpf) were observed and photographed and used for subsequent identification of genotypes (FIGS. 5A-5F).

Figure 6:
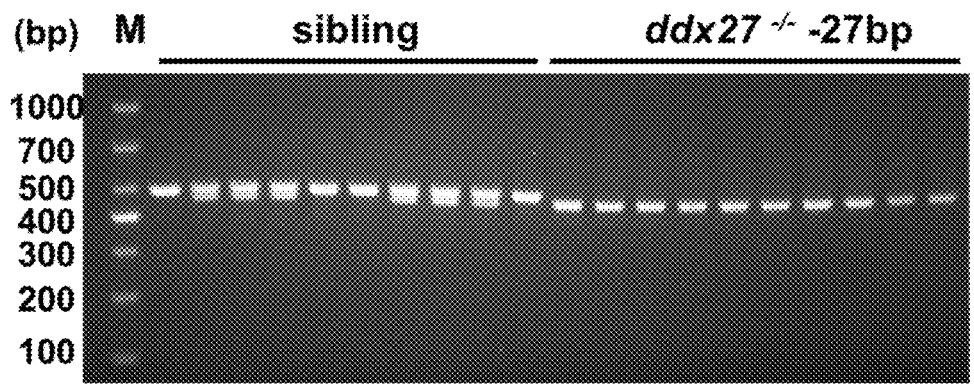
FIG. 6 is a gel electrophoresis image showing the genotype detection results of $F_2$ ddx27-27 bp zebrafish.

3.1.5 Identification of genotypes of $F_2$ Homozygous ddx27 Zebrafish Mutants (1) A single embryo of the F2 zebrafish derived from incrossing of ddx27$^{+/-}$ (−27 bp) mutants (3 dpf) was detected by electrophoresis. The genotypes were determined based on the bands. The results showed that there were 6 positive heterozygous zebrafish and 4 wild-type zebrafish, and zebrafish in the abnormal phenotype group were all homozygous, which was consistent with FIG. 5D (FIG. 6).

Figure 7:
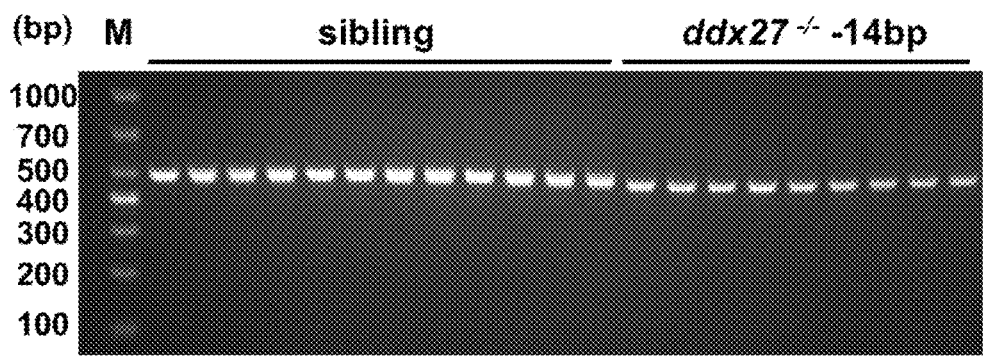
FIG. 7 is a gel electrophoresis image showing the genotype detection results of $F_2$ ddx27-14 bp zebrafish.

(2) A single embryo of the F2 zebrafish derived from incrossing of ddx27$^{+/-}$ (−14 bp) mutants (3 dpf) was detected by electrophoresis. The genotypes were determined based on the bands. The results showed that zebrafish in the abnormal phenotype group were all homozygous, which was consistent with FIG. 5E (FIG. 7).

Figure 8:
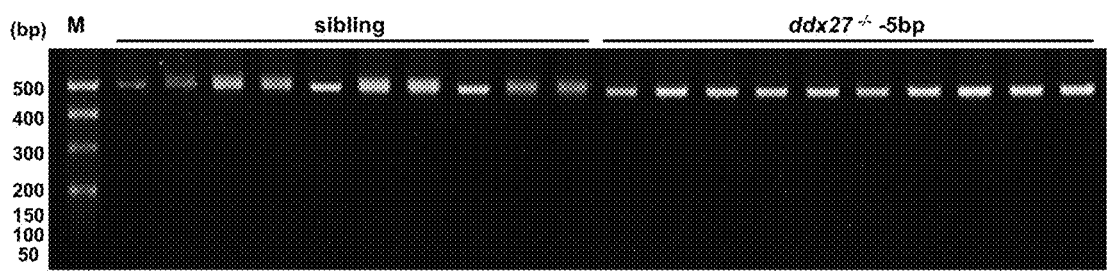
FIG. 8 is a gel electrophoresis image showing the genotype detection results of $F_2$ ddx27-5 bp zebrafish.

(3) A single embryo of the $F_2$ zebrafish derived from incrossing of ddx27$^{+/-}$ (−5 bp) mutants (3 dpf) was detected by electrophoresis. The genotypes were determined based on the bands. The results showed that zebrafish in the abnormal phenotype group were all homozygous, which was consistent with FIG. 5F (FIG. 8).

What is claimed is:

1. A method of preparing a ddx27-deletion zebrafish mutant, comprising:
   (1) determining a target on the sixth exon of a ddx27 gene in a zebrafish and designing a guide RNA (gRNA), wherein the target consists of the sequence of SEQ ID NO: 1, and the gRNA consists of the sequence of SEQ ID NO: 6;
   (2) designing and synthesizing an upstream primer T7-ddx27-sfd and a downstream primer tracr rev;
   (3) using primers T7-ddx27-sfd and tracr rev for PCR amplification with a pUC19-gRNA scaffold plasmid as a template;
   (4) transcribing and transforming the PCR product obtained in step 3 in vitro to produce the gRNA;
   (5) introducing the gRNA and a Cas9 protein into the zebrafish; and
   (6) culturing the zebrafish obtained in step 5 to obtain a zebrafish ddx27 mutant.

2. The method of claim 1, wherein in step 3, the primer T7-ddx27-sfd consists of the sequence of SEQ ID NO: 2.

3. The method of claim 1, wherein in step 3, the primer tracr rev consists of the sequence of SEQ ID NO: 3.

4. The method of claim 1, wherein step 5 further comprises:
   mixing the gRNA with the Cas9 protein to produce a mixture and microinjecting the mixture into a 1-cell stage embryo of the zebrafish; wherein a final concentration of the gRNA is 80-100 ng/μL; a final concentration of the Cas9 protein is 800 ng/μL; and a total volume of the mixture is 1 μL.

5. The method of claim 1, wherein step 6 further comprises:
   (i) examining embryos of the zebrafish introduced with the gRNA and the Cas9 protein and a wild-type zebrafish to measure ddx27 knockout efficiency so as to determine that an $F_0$ ddx27-knockout zebrafish is cultured to be an adult zebrafish;
   (ii) outcrossing the adult $F_0$ ddx27-knockout zebrafish with the wild-type zebrafish to test heritability and effective mutations, thereby screening an $F_1$ zebrafish with heritable and effective mutation for feeding to adult zebrafish; wherein an $F_1$ zebrafish ddx27 mutant is obtained by genotype identification;
   (iii) incrossing the same $F_1$ zebrafish ddx27 mutants to obtain an $F_2$ zebrafish ddx27 mutant; and
   (iv) identifying the homozygous $F_2$ zebrafish ddx27-knockout mutant as the zebrafish ddx27 mutant of stable inheritance.

6. The method of claim 5, wherein in step (i), the ddx27 knockout is examined by using a primer sequence comprising an upstream primer ddx27-F that consists of the sequence of SEQ ID NO: 4 and a downstream primer ddx27-R that consists of the sequence of SEQ ID NO: 5.

* * * * *